United States Patent [19]

Williams et al.

[11] Patent Number: 5,139,861

[45] Date of Patent: Aug. 18, 1992

[54] PROCESS FOR BONDING BLENDS OF CELLULOSIC PULP AND FUSIBLE SYNTHETIC PULP OR FIBER BY HIGH-SPEED DIELECTRIC HEATING AND PRODUCTS PRODUCED THEREBY

[75] Inventors: Kenneth R. Williams, Landenberg, Pa.; Cornelius G. Fitzgerald, St. Petersburg, Fla.

[73] Assignee: E. I. Du Pont de Nemours and Company, Wilmington, Del.

[21] Appl. No.: 779,533

[22] Filed: Oct. 18, 1991

Related U.S. Application Data

[63] Continuation-in-part of Ser. No. 541,569, Jun. 21, 1990.

[51] Int. Cl.$^5$ ............................................. D04H 1/58
[52] U.S. Cl. ................................ 428/288; 156/73.1; 156/73.2; 428/280; 428/296; 428/326; 428/327; 428/913; 604/374; 604/375; 604/377; 604/379
[58] Field of Search ........................... 156/73.1, 73.2; 428/288, 296, 326, 327, 913, 280; 604/374, 375, 377, 379

[56] References Cited

U.S. PATENT DOCUMENTS

| | | | |
|---|---|---|---|
| 2,550,006 | 4/1951 | Dreyfus | 154/126.5 |
| 3,287,474 | 4/1966 | Harrington, Jr. | 264/25 |
| 3,966,519 | 6/1976 | Mitchell et al. | 156/73.1 |
| 4,357,188 | 11/1982 | Mochida et al. | 156/180 |
| 4,401,708 | 8/1983 | Paul | 428/198 |
| 4,659,614 | 4/1987 | Vilate | 428/296 |
| 4,784,892 | 11/1988 | Storey et al. | 156/73.1 |
| 4,904,520 | 2/1990 | Dumas et al. | 428/296 |

FOREIGN PATENT DOCUMENTS

| | | |
|---|---|---|
| 8931173 | 3/1989 | Australia . |
| 73018943 | 8/1977 | Japan . |
| 52-118093 | 10/1977 | Japan . |
| 56-069149 | 6/1981 | Japan . |
| 59-062111 | 4/1984 | Japan . |
| 64-002648 | 1/1989 | Japan . |
| 1092373 | 11/1967 | United Kingdom . |

OTHER PUBLICATIONS

"Cellulose and Cellulose Derivatives", Part I, E. Ott & H. Spurlin, Editors, High Polymer Series, vol. 5, Interscience, pp. 400–402 (1954).
Ramo et al., "Fields and Waves in Communications Electronics," John Wiley, 2nd ed., p. 490 (1984).
Marcuvitz, "The Waveguide Handbook", MIT Radiation Laboratory Series, vol. 10 (1951).

*Primary Examiner*—James J. Bell

[57] ABSTRACT

A process is disclosed for bonding blends of cellulosic fluff pulp and fusible synthetic pulp or fiber having a melting point less than 250° C., by high-speed dielectric heating. The process works in the absence of any dielectric sensitizing material, but requires the resulting blend have a density between 0.005 and 0.50 g/cc so that the blend can be bonded in less than 15 seconds. The process is useful for producing disposable baby diapers, adult incontinence products and feminine pads.

12 Claims, 7 Drawing Sheets

PROCESS FOR BONDING BLENDS OF CELLULOSIC PULP AND FUSIBLE SYNTHETIC PULP OR FIBER BY HIGH-SPEED DIELECTRIC HEATING AND PRODUCTS PRODUCED THEREBY

CROSS REFERENCE TO RELATED APPLICATION

This application is a continuation-in-part of application Ser. No. 07/541,569 filed Jun. 21, 1990.

FIELD OF THE INVENTION

The invention relates to a process for bonding blends of dry cellulosic fluff pulp and fusible synthetic pulp or fiber by high-speed dielectric heating in the absence of any dielectric sensitizing material. The invention also relates to products produced by the bonding process.

BACKGROUND OF THE INVENTION

The use of disposable hygienic products, such as baby diapers, adult incontinence products and feminine napkins, is widespread in developed nations. All of these products are designed to absorb body fluids efficiently and at low cost. Typically, the principal absorbent material used in the core of these products is cellulosic fluff pulp. The cellulosic fluff pulp is usually obtained by defibering a pulp sheet in a hammermill or a pin mill. Although cellulosic fluff pulp is relatively inexpensive, its high weight percentage in the final product makes it the major material cost of the hygienic disposable product. Additionally, increasing environmental concerns dictate that disposable products be lower in volume and weight so that they don't take up as much landfill space. As a result, there is an increasing need to reduce the quantity of cellulosic fluff pulp in disposable products.

One technique that has found widespread acceptance in the baby diaper industry is to incorporate one or more super absorbent polymers (hereinafter "SAP") into the cellulosic fluff pulp. The absorption capacity index (i.e., g fluid absorbed/ g of absorbent) for diaper cores containing SAP is significantly greater than that for cores containing no SAP, so the total core weight of the disposable product can be reduced while still maintaining equivalent total absorption.

Another technique for reducing the quantity of cellulosic fluff pulp in the final disposable product is to thermally bond the cellulosic fluff pulp with a small amount (e g., 2-30 wt. %) of a fusible synthetic pulp or fiber that is intermixed therewith. The resulting bonded pulp has greatly increased tensile and compressive strength over unbonded pulps. In addition, fluid absorption, particularly under load, is also increased. As a consequence of such bonding, the core weight of the disposable product can be reduced significantly, while still maintaining equivalent total absorption.

In such bonding applications, a thermal bonding device is necessary to realize reductions in core weight. Since the fluff pulp core is created during the manufacturing process, it is highly desirable for the thermal bonding device to be an integral part of the process. Although it is possible to make bonded cores separately, and then to combine them on the production line with other elements of the disposable product, such steps are economically unrealistic. Several specific bonding techniques have been proposed, but there are significant speed and safety constraints that have sharply limited commercialization of these techniques.

The presently preferred bonding technique practiced by the disposable art utilizes a "through air" system in which air, heated above the fusion temperature of the fusible synthetic pulp or fiber, is introduced into a substantially closed container. The intermixed pulp material travels around a perforated drum or on a mesh belt which is under vacuum, so that heated air is drawn through the pulp material thereby heating it above the fusion temperature of the synthetic pulp or fiber. The bonding step is critical because, at the operating speeds of present day production lines, fusion must be accomplished in a fraction of a minute, ideally two seconds or less. Fusion time can be increased by increasing the length of travel in the thermal bonder, but this approach leads to excessively large and costly bonding units.

Another alternative is to use radiant energy to bond the pulp material. However, radiant heating creates a significant safety hazard because the equipment utilized operates at temperatures above the ignition point of cellulose.

Still another technique is to use dielectric heating, but there are formidable problems with the use of this type of technology. Dielectric heating involves rapid and uniform heating throughout a nonconducting material by means of a high-frequency electromagnetic field. Commonly, this includes radio frequency (hereinafter "RF") and microwave energy. Most commercially available RF or microwave heaters are large and the product moves through them slowly. Power can be increased, but there is a limitation in this application since no arcing can be tolerated due to the extreme fire danger produced by pulp fines floating in the atmosphere. Therefore, they are not suited for an in-line thermal bonding operation useful for manufacturing hygienic disposable products.

Finally, the fusible synthetic pulp or fibers (e.g., polyolefins and polyesters) have low dielectric loss factors which make them unreactive at radio frequencies. Existing commercially-marketed synthetic fibers in general, and polyester fibers in particular, do not heat up in an oscillating electromagnetic field and cannot be thermally bonded. Indeed, polyesters are good insulators and have low dielectric or inductive loss. This property is why polyesters are useful in capacitors.

In order to overcome the above-noted problem, the costly step of incorporating a polar material in the manufacture of the fusible synthetic pulp or fiber has been considered necessary to achieve rapid dielectric heating to fusion temperatures. For example, the approach adopted in U.S. Pat. No. 4,401,708, directed to a method of bonding nonwoven fabrics using microwave energy and a polar trichloroacetic acid solvent, presents significant control problems in applying the solvent to appropriate pulp or fiber locations without excessive degradation of the pulp or fiber upon prolonged exposure to the solvent. Control problems lead to nonuniformly bonded products.

Although techniques for thermally bonding absorbent fluff pulp cores have been known for many years, their adoption by the hygienic disposable product industry has been very slow. Reasons for this situation include the unsatisfactory size, cost and safety of commercially available bonding units.

As a result, what is needed is a process to improve the speed of thermal bonding over what has previously been possible commercially. Another objective is to overcome some of the limitations that have been apparent, and even inherent, in various prior art commercial bonding techniques. Moreover, the cost-effectiveness of the process is always an important objective for any commercial operation.

Other objects and advantages of the present invention will become apparent to those skilled in the art upon reference to the attached drawings and to the detailed description which hereinafter follows.

SUMMARY OF THE INVENTION

In accordance with the present invention, there is provided a process for bonding blends of cellulosic fluff pulp and fusible synthetic pulp or fiber by high-speed dielectric heating. The process comprises, as a first step, blending a dry cellulosic fluff pulp with a fusible synthetic pulp or fiber having a melting point less than 250C., such that the resulting pulp blend has a density of between about 0.005 and 0.50 g/cc and comprises between 5-98 parts cellulosic fluff pulp and between 2-95 parts fusible synthetic pulp or fiber. Thereafter, the blend is bonded in less than 15 seconds by dielectric heating. Bonding occurs at temperatures which are apparently below the melting point of the fusible synthetic pulp or fiber when instrumentally measured inside the blended material.

The invention recognizes that fusible synthetic pulps and fibers, preferably polyethylene, having a melting point less than 250 C, which are normally unreactive to high frequency electromagnetic fields like radio frequencies and microwave energy, can be bonded in the absence of dielectric sensitizing materials when intimately mixed with a dry cellulosic fluff pulp.

In another aspect of the invention, there is provided a dielectrically bonded article having a density between about 0.005 and 0.50 g/cc, comprising 5-98 parts of a cellulosic fluff pulp and 2-95 parts of a fusible synthetic pulp or fiber having a melting point less than 250 C. The tensile strength of the interior of the bonded article is at least 120% greater than the tensile strength of any surface portion of the bonded article. The bonded article of the invention is particularly useful as an absorptive core in disposable hygienic products, preferably baby diapers, adult incontinence products or feminine pads. In addition, the bonded article may also be used as furniture padding, cushioning material or polishing pads.

As used herein, "high-speed dielectric heating" means that the blended cellulosic fluff pulp and fusible synthetic pulp or fiber can be bonded by a high frequency electromagnetic field in less than 15 seconds, preferably within 1 to 2 seconds. Non-limiting examples that can produce the desired high frequency electromagnetic field include radio frequencies ("RF") and microwave energy.

As used herein, "dry" means that the cellulosic fluff pulp has less than 6 wt.% moisture but contains "bound water" as defined in Cellulose and Cellulose Derivatives, Part I, by E. Ott and H. Spurlin, Editors, High Polymer Series, Vol. 5, Interscience, pp. 400-402 (1954).

DETAILED DESCRIPTION OF PREFERRED EMBODIMENTS

In accordance with the invention, an intimately blended pulp is prepared by feeding a refined polyethylene pulp, or other fusible synthetic pulp or fiber, in sheet form into a hammermill along with one or more dry cellulosic pulp sheets. These sheets are typically in roll form. The hammermill produces an intimately blended polyethylene and cellulosic fluff pulp. Preferably, for polyethylene, the pulps are blended so that the hammermill yields a fluff blend containing 2-30 parts polyethylene pulp and 70-98 parts cellulosic fluff pulp. The resulting pulp blend is conducted to a vacuum former where a low density (0.005-0.50 g/cc) fluff pulp web is built up on a continuously moving screen.

Preferably, the cellulosic pulp sheet comprises wood pulp or cotton linters, however, other suitable cellulosic or cotton fibers are also useful in the invention. A suitable wood pulp useful in the invention is commercially available from Weyerhaeuser Paper Co., Federal Way, Washington as New Bern (NB) 316 cellulose pulp. A suitable polyolefin pulp useful in the invention is commercially available from E. I. du Pont de Nemours & Co., Wilmington, Del. under the trademark Plexafil TM. It should be noted that other fusible synthetic pulps or fibers may be substituted for polyethylene for purposes of the invention. Non-limiting examples include, polypropylene, polyvinyl alcohol, polyester, 6 nylon and 66 nylon.

Alternatively, the cellulosic and polyethylene pulp blend may contain from 0 to 30 parts of a polar material, such as a super absorbant polymer (SAP). Additionally, other adjuvants, such as odor control materials, may be added to the blended pulp to meet customer needs. However, it is to be understood that these materials are not critical to the invention since dielectric bonding will occur to the same extent with or without them.

The resulting continuous web is transferred to an insulative belt which is radio frequency insensitive and passed through a radio frequency applicator cavity. The applicator cavity as used herein refers to a transverse electric cavity or TE101 mode microwave cavity. The TE101 mode cavity is referenced in Ramo, Whinnery and Duzer, "Fields and Waves in Communications Electronics", John Wiley, 2nd edition, page 490 (1984) and further described in Marcuvitz, "The Waveguide Handbook", MIT Radiation Laboratory Series, Volume 10 (1951). The microwave energy and applicator cavity design are adjusted so that bonding occurs in the cavity in less than 15 seconds. Preferably, bonding occurs within 1 to 2 seconds after application of the microwave energy.

It is well known that materials with a high dielectric loss factor (i.e., polar materials) will heat up in a high frequency electromagnetic field. Further, it is known that non-polar materials, such as polyolefins and polyesters, can be heated by conduction by applying dielectric sensitizing polymers which are polar to the surface or within the body of the non-polar material. Such sensitizing materials are commercially available for both RF (less than 300 MHz) and microwave frequency (greater than 300 MHz) applications.

The invention will be further described by reference to the following non-limiting examples. As used herein, all percentages are by weight unless otherwise indicated.

EXAMPLE 1

A dielectric sensitizing polymer, commercially available from the Struktol Corporation of Stowe, Ohio under the tradename Frequon C-10, was applied to numerous sheets of Plexafil TM polyolefin pulp so as to give add-on levels of 1%, 5% and 10% Frequon C-10. Plexafil TM is a trademark for a commercially available polyolefin pulp from E. I. du Pont de Nemours & Co., Wilmington, Del. The pulp was defibered in a laboratory blender for 1 minute to yield a low density, 0.02 g/cc fluff. The fluff pulp samples were subsequently placed in a W.T. LaRose model CCH-8.5 dielectric heater operating in a RF range of 90-91 MHz. A nonintrusive probe made by the Luxtron Corporation (LUXTRON Model 755 Fluoroptic Thermometer) was inserted into the fluff structure and the temperature was measured as a function of time. These measurements are plotted in FIG. 1.

Figure 1:
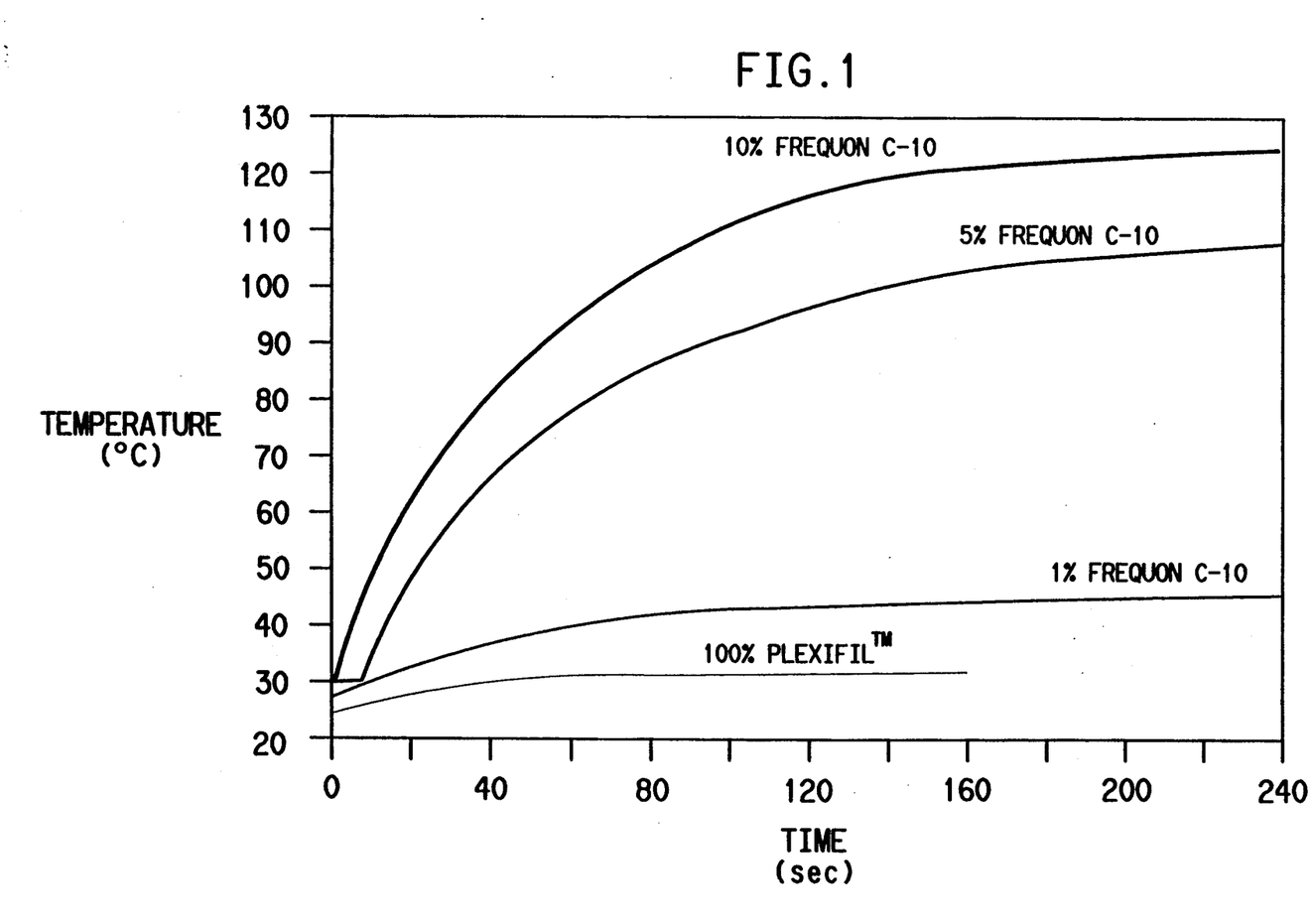
FIGS. 1-7 show curves plotting temperature against time for various fiber blends as described hereinafter.

FIG. 1 shows that the temperature of the polyolefin pulp with no Frequon C-10 present (i.e., 100% Plexafil TM) remains almost unchanged over 160 seconds. However, applying 1%, 5% and 10% concentrations of Frequon C-10 to the surface causes a continuous rise in temperature up to 240 seconds. The rate of temperature rise increases with increasing Frequon C-10 concentration.

EXAMPLE 2

Figure 2:
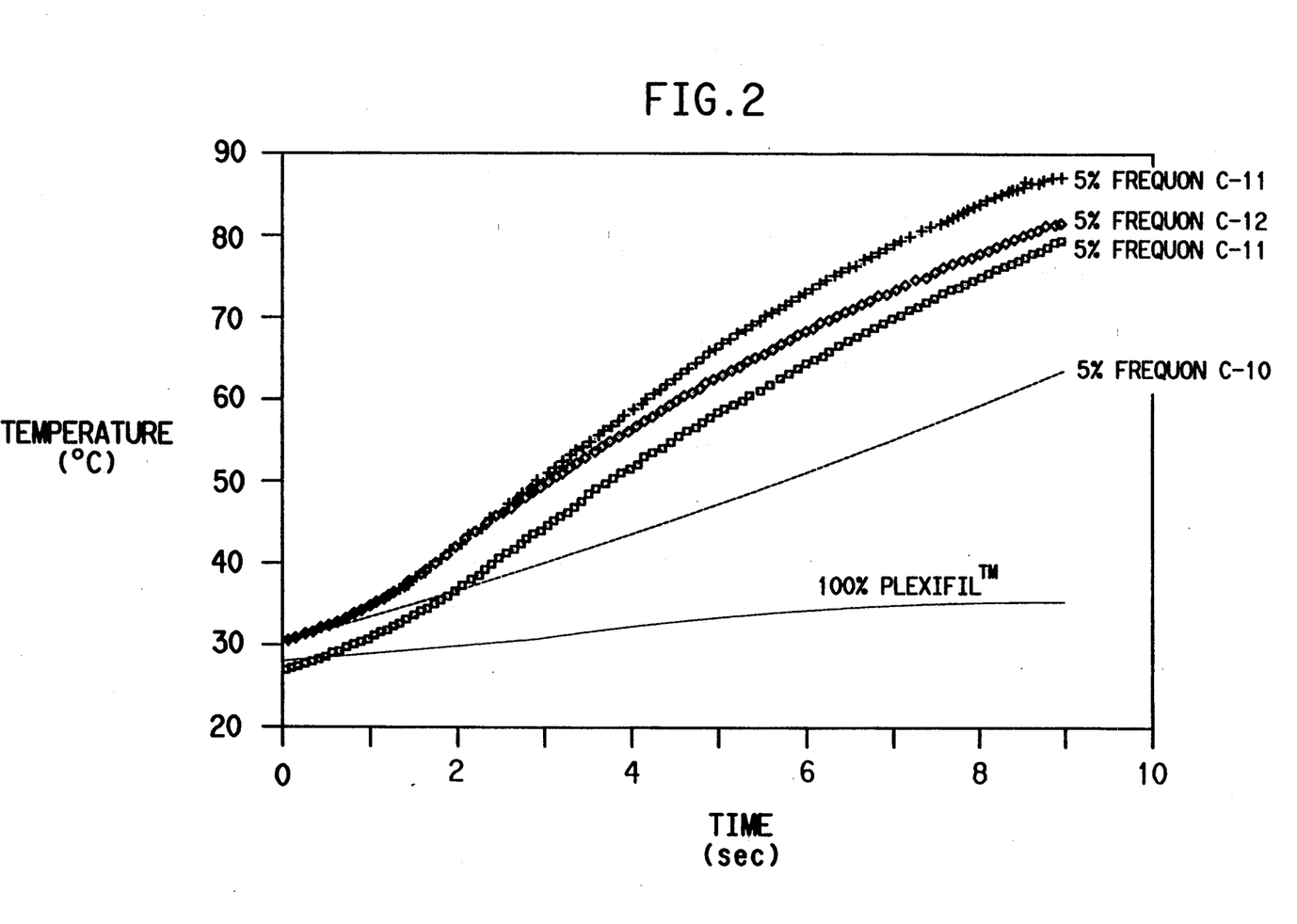

This example mirrors Example 1, except that the temperature versus time behavior was observed using microwave frequencies. The microwave unit consisted of a rectangular cavity resonator operating in a TE1O1 mode where the electric field is uniform across the transverse direction and has one standing wave condition (peak) in the machine and height directions. The unit was supplied with a power generator operating at a frequency of 925 MHz and approximately 400 watts. The presence of various organic polymer activators (i.e., dielectric sensitizing polymers) at 5% concentration, Frequon C-10, C-11, and C-12 (all commercially available through the Struktol Corporation of Stowe, Ohio), caused a significant rise in temperature, while temperature was only modestly raised when no Frequons were present. These experiments are set forth in FIG. 2 and show that pure polyolefin pulp in fluff form (i.e., 100% Plexafil TM) cannot be heated significantly in the absence of high dielectric loss materials, like Frequon C-10, C-11 or C-12.

EXAMPLE 3

In this example, blends of cellulose and fusible pulps or fibers were defibered by processing them in a laboratory blender. Thereafter, the blended pulp was vacuum formed into a low, approximately 0.02 g/cc, density web on a screened 7.5 cm diameter cavity. The resulting web was compressed by a plate placed on top of the blended pulp to a desired final density of about 0.09 to 0.12 g/cc prior to bonding in a dielectric heater.

Figure 3:
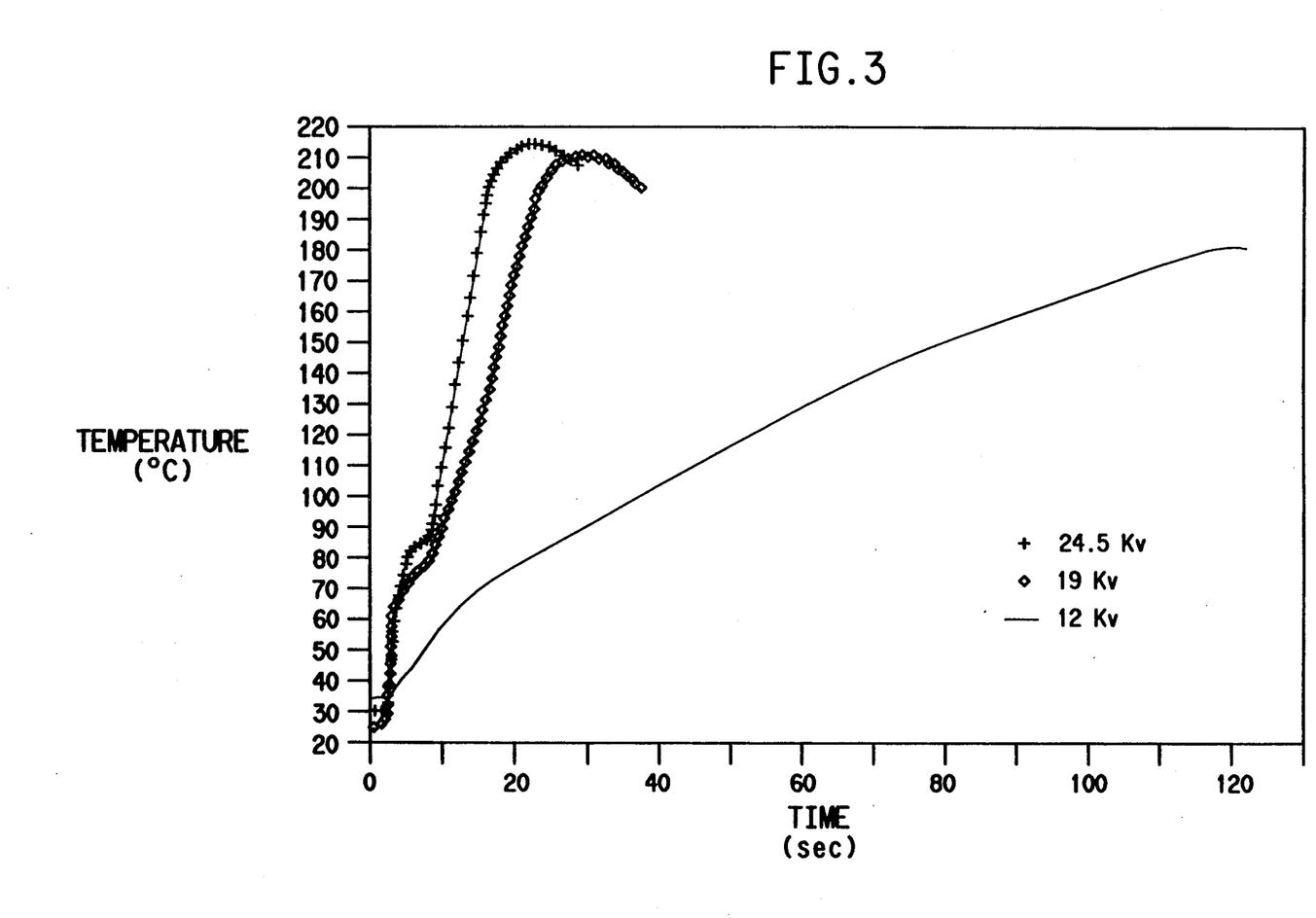

Referring now to FIG. 3, the temperature rise associated with Example 3 is shown for a nonwoven fluff composed of 85 parts Weyerhaeuser NB 316 lb. kraft cellulose pulp and 15 parts Plexafil TM which contained 1% Frequon C-10 on its surface. At 12 KV, in the same RF unit as was used for Experiment 1, the temperature rose in 60 seconds to 130 C compared to 40 C in FIG. 1. Higher operating voltages, 19 and 24.5 KV respectively, showed further rapid increases in recorded temperature in the blended pulp. The blend of cellulose fluff and Plexafil TM with 1% Frequon C-10 showed a more rapid temperature rise than a fluff of Plexafil TM alone with 1% Frequon C-10 (Example 1).

EXAMPLE 4

Figure 4:
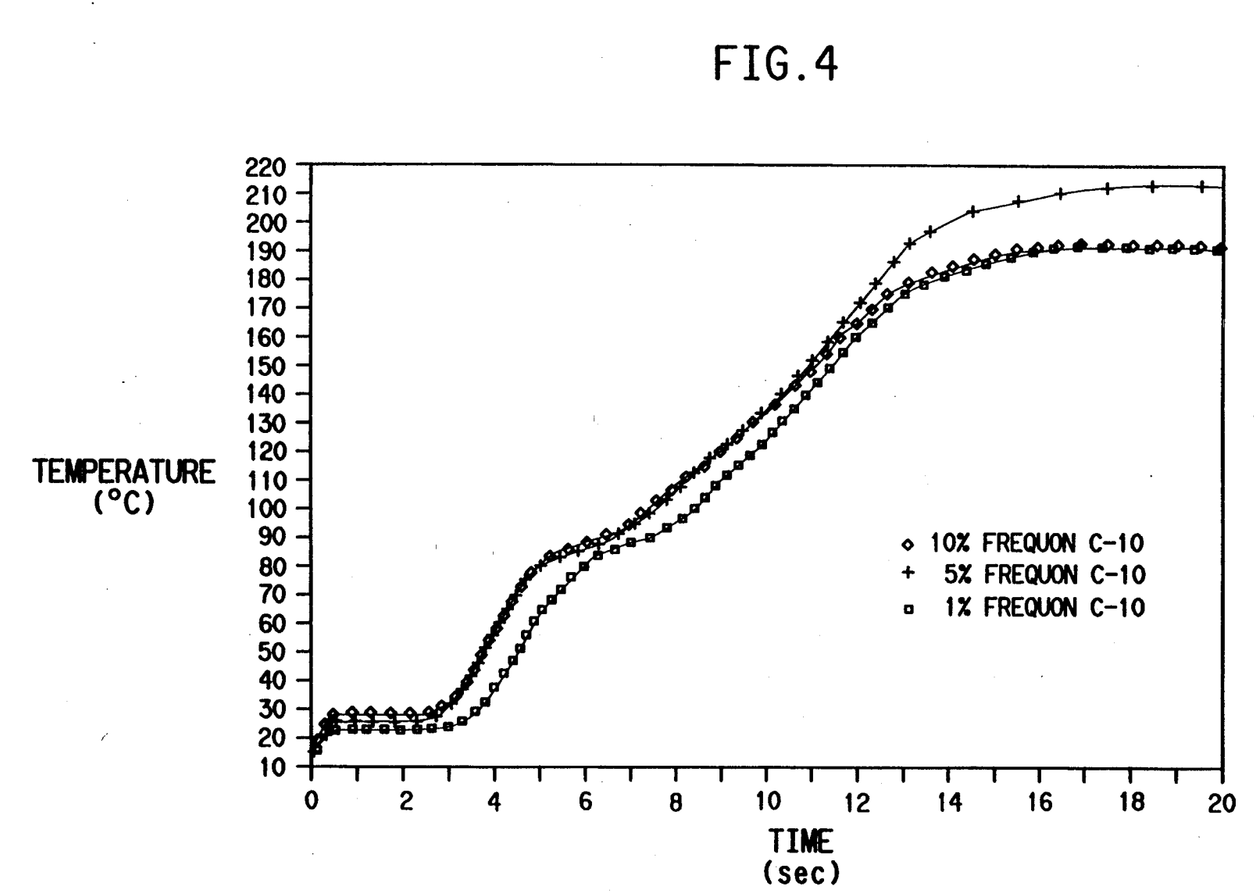

In this example, varying amounts of Frequon C-10 were applied to Plexafil TM sheets as described in Example 1. Treated Plexafil TM was processed with Weyerhaeuser NB 316 cellulose pulp as described in Example 3 and then subjected to RF radiation in a W.T. LaRose C220/100 dielectric heater at 15 KV peak voltage and 77.5 MHz frequency. Parallel plate electrodes were used. FIG. 4 shows similar temperature profiles for a 0.08 g/cc fluff blend of 85 parts Weyerhaeuser pulp and 15 parts Plexafil TM in which the Plexafil TM contained varying amounts of Frequon C-10, in 1%, 5% and 10% concentrations on its surface. This is to be contrasted with the large temperature differences when Frequon concentration was varied on 100% Plexafil TM fluff shown in FIG. 1.

EXAMPLE 5

In this example, fluff composites were made, as in Example 2, of kraft pulp (Weyerhaeuser NB 316)/Plexafil TM pulp, 85/15 and 0.060-0.075 g/cc density, with and without Frequon C-10 on the surface of the Plexafil TM. The composites were dielectrically heated in a W.T. LaRose C220/100 RF unit at 15 KV peak voltage and 77.5 MHz frequency. Table 1 shows probe temperature as a function of time for samples A, E, F, and J both during RF treatment and after the RF unit was turned off.

TABLE 1

|  | Sample A | Sample E | Sample F | Sample J |
|---|---|---|---|---|
| Frequon Conc. on Plexafil TM (%) | 0 | 5 | 0 | 5 |
| Radio Frequency Application Time (sec.) | 2 | 2 | 4 | 4 |

| Time From Start of R.F. Application (sec.) | Probe Temp. (C.) | | | |
|---|---|---|---|---|
| 0 | 25.7 | 26.8 | 27.7 | 25.3 |
| 1 | 45.9 | 56.4 | 66.8 | 37.7 |
| 2 | 79.8 | 86.8 | 99.8 | 78.8 |
| 3 | 77.2 | 81.5 | 100.6 | 94.9 |
| 4 | 73.1 | 78.9 | 117.2 | 107.4 |
| 5 | 72.5 | 79.6 | 122.3 | 117.0 |
| 6 | 73.7 | 80.9 | 129.5 | 126.1 |
| 7 | 79.1 | 81.6 | 134.1 | 132.6 |
| 8 |  | 82.1 | 137.3 | 136.5 |
| 9 |  | 82.1 | 138.9 | 138.7 |
| 10 |  | 81.7 | 140.1 | 140.8 |
| 11 |  |  | 140.8 | 141.5 |

The data show only modest differences in temperature rise between samples with and without Frequon C-10 on the Plexafil TM. Temperature rise is controlled by the length of time RF energy is applied to the samples. Subjective determination of bonding showed that all samples exhibited some degree of bonding despite the low recorded temperature for samples A and E that never reached the fusion temperature of linear polyethylene. Samples F and J showed subjectively good bonding although the linear polyethylene fusion temperature was just reached for a few seconds. With a two second cycle time, the maximum temperature recorded occured at the end of the RF treatment period. With a four second RF cycle time, the temperature continued to rise for several seconds after the RF unit was turned off. When similar density samples were heated by convection in an oven, there was only modest bonding even after 5 minutes of treatment. This example shows that temperature rise and bonding of a cellulose fluff/fusible polyolefin pulp blend occurs to the same extent with or without the presence of a high dielectric loss material on the fusible polyolefin pulp surface.

EXAMPLE 6

Figure 5:
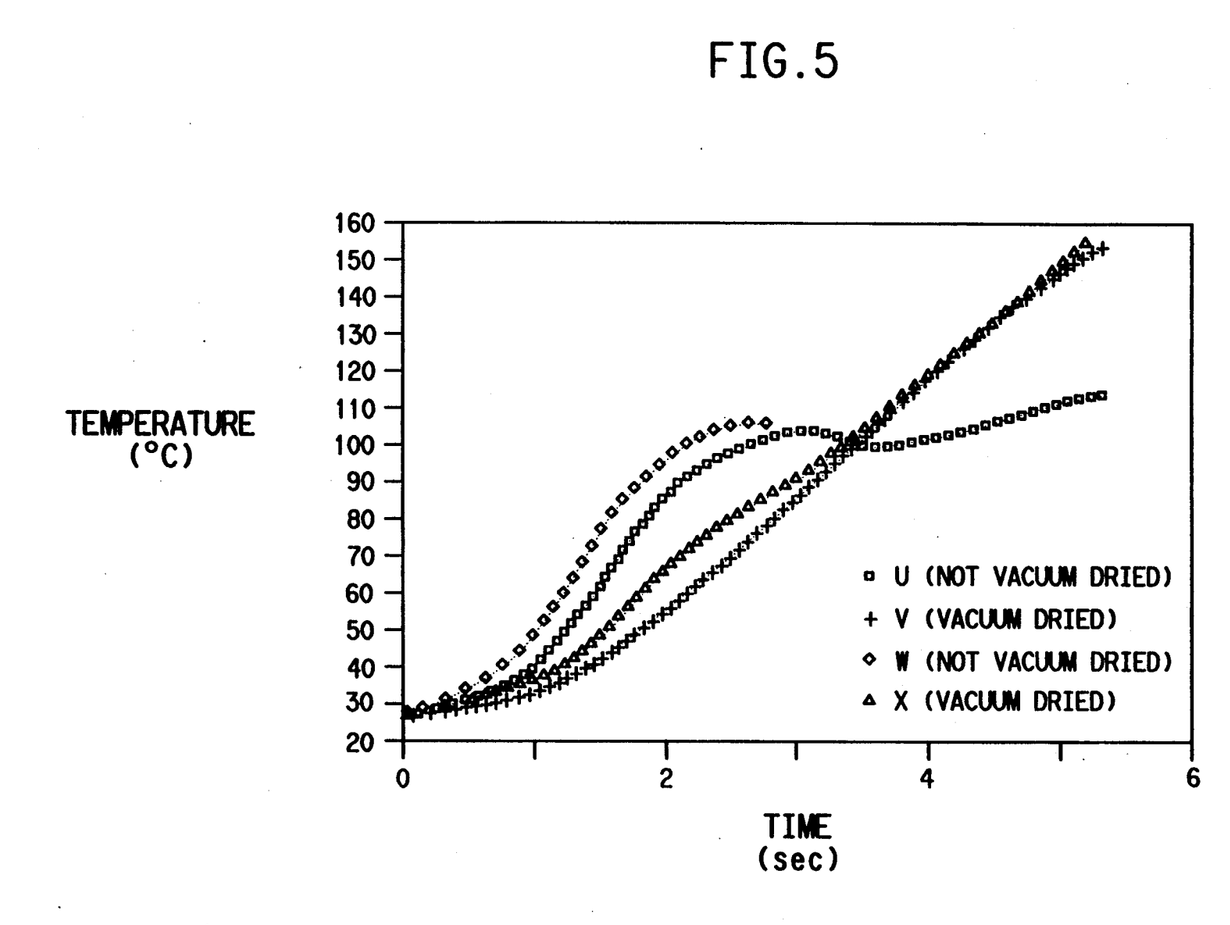

In this example, samples U, V, W and X were prepared by the same procedure as in Example 3. Samples U and V were made of 90 parts cellulose fluff, 10 parts Plexifil TM and 10 parts Stockhausen W40158 SAP (commercially available from the Stockhausen Corporation of Greensboro, N.C.). Samples W and X were made of 90 parts cellulose fluff and 10 parts Plexafil TM. The samples had densities ranging from 0.06 to 0.025 g/cc and were subjected to an 8 second RF cycle time. FIG. 5 shows that there is a difference in the temperature versus time curves for samples that were vacuum dried (V and X) prior to treatment, and those that were not vacuum dried (U and W). The vacuum dried samples show a reasonably constant rate of temperature rise over much of their cycle time, reaching a probe temperature well above the fusion temperature of polyethylene before the power was turned off. Under these conditions, sample V ignited. Therefore, safety considerations require that the input RF energy be adjusted so that probe temperature does not exceed 150 C while RF energy is being applied.

EXAMPLE 7

In this example, air-laid felts were prepared, as in Example 3, of 90 parts cellulose fluff pulp and 10 parts Plexafil TM, in a range of densities from 0.06 to 0.8 g/cc. All fluff systems were defibered in a laboratory blender. The samples of highest density, 0.8 g/cc, were obtained by wetting out the samples with water to make them more readily compressible. After compression, these samples were dried before testing. Table 2 illustrates the densities of the various sample numbers.

TABLE 2

| Sample No.* | Density (g/cc) | Sensitizer on Plexafil TM (%) |
|---|---|---|
| M | 0.06 | None |
| N | 0.10 | None |
| O | 0.20 | None |
| P | 0.50 | None |
| T | 0.80 | None |
| S | 0.80 | 5% Frequon C-10 |

*All samples were defibered blends of 5.0 ± 0.15 g of 90 parts kraft cellulose pulp and 10 parts of Plexafil TM.

Figure 6:
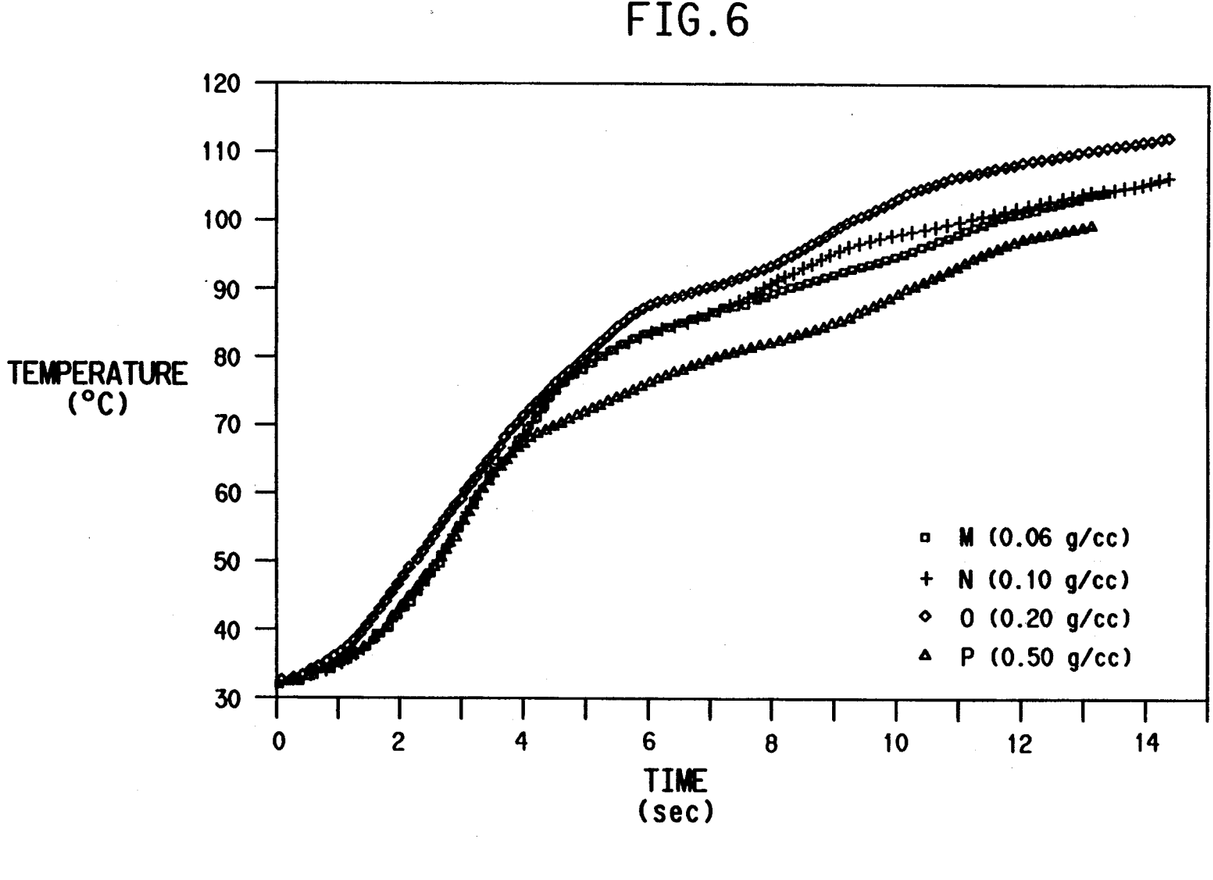
Figure 7:
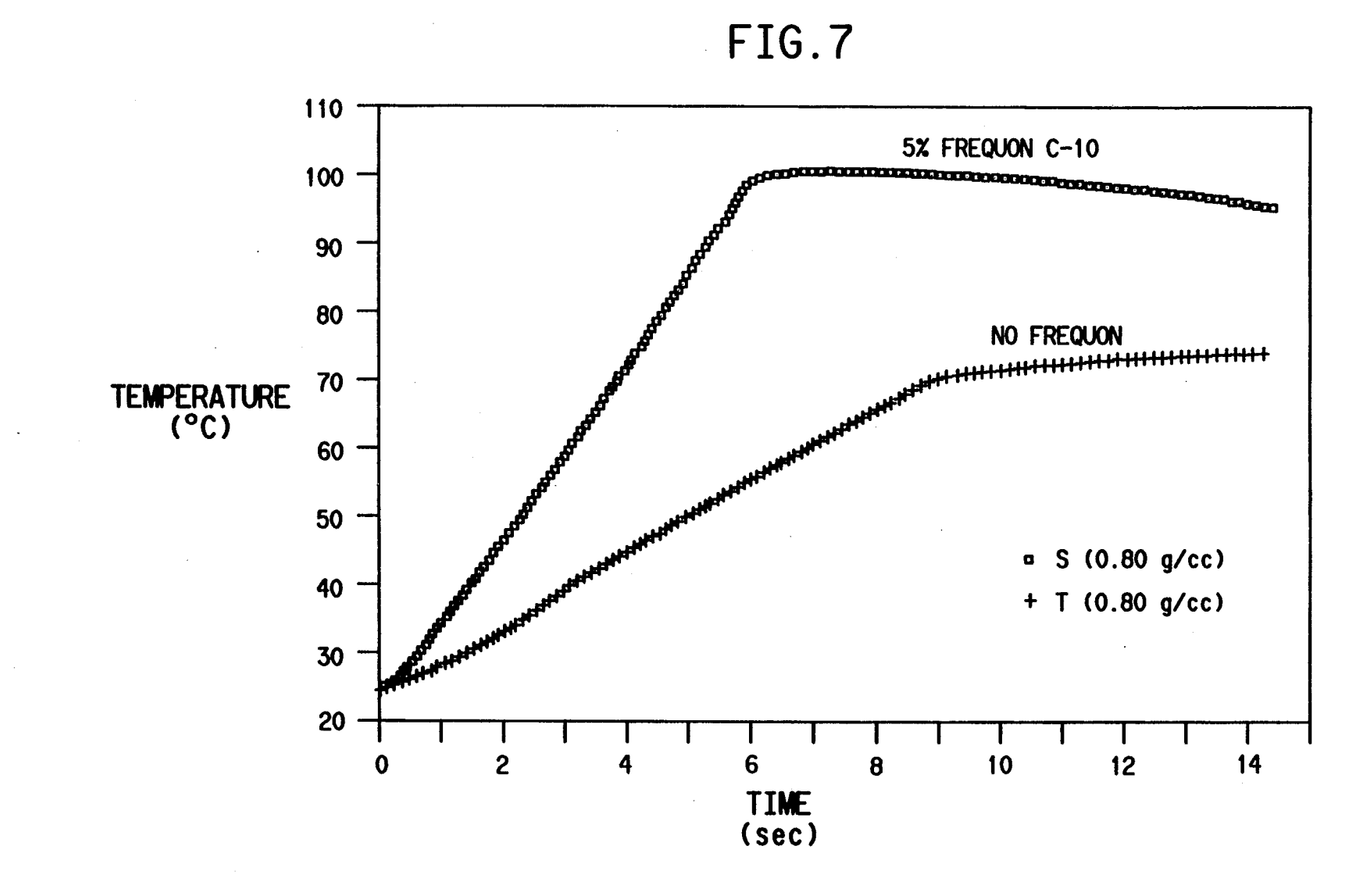

All samples were tested in a microwave applicator for 8 seconds at 922 MHz frequency and 370 watts. FIG. 6 shows similar probe temperature versus time curves for all samples up to a density of 0.5 g/cc (samples M,N,O and P). Samples of density greater than 0.5 g/cc (samples T and S), shown in FIG. 7, have a different temperature versus time profile. With these higher density samples, there is a sharp change in the slope of the probe temperature versus time curve. Further, sample S, which contained a Frequon C-10 dielectric sensitizer, showed a more rapid initial temperature rise. This is to be contrasted to the temperature versus time measurements made with lower density composite structures in which the presence or absence of Frequons on the fusible polyolefin pulp blend had little effect. Thus, sample density influences the time versus temperature relationship in microwave heating. As a result, cellulose fluff pulp and fusible pulp or fiber nonwoven blends of densities below 0.50 g/cc can be dielectrically bonded more rapidly than heavier density blended pulps and they are therefore more desirable.

EXAMPLE 8

In this example, samples were made, as in Example 3, at about 0.08 g/cc density with the following formulations:

| Sample | Cellulose (Parts) | Fusible Pulp/Fiber (Parts) | SAP* (Parts) |
|---|---|---|---|
| A | 90 | Plexafil TM -10 | 0 |
| B | 96 | Plexafil TM -4 | 10 |
| C | 90 | Pulpex ® E-338**-10 | 0 |
| D | 90 | Dacron ® Type 271***-10 | 0 |

*Available from Stockhausen Corporation of Greensboro, North Carolina as SAP W40185.
**A polyolefin pulp commercially available from Hercules, Incorporated of Wilmington, Delaware.
***A sheath/core, bicomponent polyester fiber available from E. I. du Pont de Nemours & Co., Wilmington, Delaware. The copolyester in the sheath has a melting point of 110° C.

All samples were treated in a W.T. LaRose C220/100 RF heater at 15 KV peak voltage and 77.5 MHz frequency. All samples showed good bonding after treatment.

EXAMPLE 9

In this example, air-laid webs were produced in 7.5 cm diameter disk form from 85 parts Weyerhaeuser NB 316 pulp and 15 parts of Plexafil TM pulp. The disks were then thermally bonded at a density of 0.08 g/cc in two ways. The two ways included (1) heating the disks in a laboratory press at fixed caliper with the upper platten at 154 C and the lower platten at 150 C and (2) heating the disks in an RF radiation unit as described in Example 4.

Softness and hand of the disks bonded by the two techniques were readily distinguishable. The dielectrically-bonded disks had soft surfaces and firm interiors, while the press-bonded disks showed the opposite characteristics. In fact, the press-bonded disks showed the greatest degree of bonding on the surfaces. This subjective difference can also be characterized quantitatively by measuring the tensile properties of the bonded web at the surface and in the interior of the disk. The following procedure was used:

After the disks were thermally bonded, they were cut into three 7.5 cm diameter wafers of approximately equal thickness and equal weight. One wafer was cut from the middle zone of the original disk while each of the other two wafers contained one of the outer surfaces of the original disk. In other words, there were two wafers cut from the outside and one wafer from the inside of the original disk. These wafers were then tensile tested at 20 C and 60% relative humidity using an Instron unit with a 3.75 cm jaw spacing and a 1.25 cm/min. rate of extension. The sides of the wafers were trimmed so that rectangular specimens of dimensions 5 cm × 3.75 cm were tested. The breaking load and weight of the disks were determined. The ratio of the strength of the inside wafer to the strength of the outside wafer (all normalized to equivalent wafer weight) was calculated. Table 3 illustrates the differences between the press bonded disks and the RF bonded disks.

TABLE 3

| | Strength Ratio (Inside Wafer/Outside Wafer) | | |
|---|---|---|---|
| | Press Bonded | RF Bonded | Bonding Time (sec.) |
| | 0.53 | 2.12 | 8 |
| | 0.84 | 1.46 | 8 |
| | 0.88 | 1.29 | 8 |
| | 0.45 | | |
| | | 1.12 | 4 |
| | | 1.85 | 4 |
| Avg. | 0.68 | 1.57 | |

The data show that RF bonded specimens are characterized by greater thermal bonding in the interior, while bonding by conduction in a press causes the surface to be more thoroughly bonded. In fact, the bonded specimens produced by the inventive process have an interior tensile strength that is at least 120% of the tensile strength of any outer surface of the bonded specimens. The soft outer surfaces of the dielectrically bonded specimens make them particularly preferred as the absorptive core in hygienic disposable products such as baby diapers.

EXAMPLE 10

In this example, the peak temperature of cellulose fiber was estimated by determining the tensile strength of fusible synthetic fiber/cellulose fluff pulp specimens containing 6 mm synthetic fibers of differing melting points. It is believed that significant specimen bond strength required a cellulose pulp peak temperature at least as high as the synthetic fiber melting point used in the specimen, in order to create a fused fiber network.

The specimens were comprised of low density defibered cellulose pulp/synthetic fusible fiber blends. Specimen composition consisted of the synthetic fusible fiber weight percentage listed in Table 4. The remainder of the specimen Was Weyerhaeuser NB-316 kraft pulp. Thermal bonding was accomplished in a LaRose R.F. unit, as in Example 8. The degree of bonding was determined by tensile testing the specimens using a Thwing Albert tensile tester (jaw spacing 7.5 cm; sample width 2.5 cm; crosshead speed 1.25 cm/min.). Controls were bonded at a fixed caliper in a press at two temperatures, namely 155 C and 190 C, for five minutes to establish the temperature required to get significant specimen strength.

TABLE 4

| Specimen No. | Syn. Fiber % | Syn. Fiber Type | M.P. (C) | Bonding Method | Bonding Time | Bonding Temp. | Density (g/cc) | Tensile Strength |
|---|---|---|---|---|---|---|---|---|
| 7-15-1C | 10 | Polyester Copolymer (15CX) | 190 | R.F. | 6 sec. | — | 0.069 | 222 g/g |
| 7-18-1A | 10 | Polyester Copolymer (15CX) | 190 | Press | 300 sec. | 155 C. | 0.065 | 24 g/g |
| 7-18-1B | 10 | Polyester Copolymer (15CX) | 190 | Press | 300 sec. | 190 C. | 0.070 | 165 g/g |
| 8-21-1A | 10 | 2G/T Polyester* | 242 | R.F. | 10 sec. | — | 0.050 | 179 g/g |
| 8-21-2A | 45 | 2G/T Polyester* | 242 | R.F. | 10 sec. | — | 0.080 | 538 g/g |
| 7-18-1C | 10 | 2G/T Polyester* | 242 | Press | 300 sec. | 190 C. | 0.065 | 38 g/g |
| 9-11-1A | 10 | 6,6 Nylon** | 242 | R.F. | 10 sec. | — | 0.050 | 227 g/g |

*Fiber designation "Dacron" T-257 commercially available from E. I. du Pont de Nemours & Co., Wilmington, Delaware.
**Fiber designation Nylon T-280 commercially available from E. I. du Pont de Nemours & Co., Wilmington, Delaware.

In Table 4, polyester copolymer fiber (Specimen No. 7-15-1C designated Fiber Type 15CX) was blended into a low density fluff form (90 wt % NB-316 kraft fluff pulp/10 wt.% 15CX fiber). It showed a high degree of bonding (i.e., 222 g/g of specimen) when treated in the LaRose unit for 6 seconds. Control specimens (Specimen Nos. 7-18-1A and 7-18-1B), press bonded at fixed caliper at 155 C and 190 C, show that higher press temperature is required for significant bonding, however, the strength level was not equal to Specimen No. 7-15-1C which was treated for 6 seconds in the LaRose R.F. unit.

Similar results were obtained with cellulose fluff pulp pads containing either a 2G/T polyester fiber or a 6,6 nylon fiber when subjected to a 10 second R.F. cycle. Specimen No. 8-21-1A (90 wt.% NB-316 kraft pulp/10 wt.% Dacron T-257) showed a tensile strength of 179 g/g, while Specimen No. 8-21-2A (55 wt.% NB-316 kraft pulp/45 wt.% Dacron T-257) had a tensile strength of 538 g/g. Specimen No. 9-11-1A (10 wt.% 6,6 nylon/90 wt.% NB-316 kraft pulp) had a tensile strength of 227 g/g.

When heated at fixed caliper for 300 seconds at 190 C in a press, a 90 wt.% NB-316 kraft pulp/10 wt.% Dacron T-257 fluff pulp specimen (Specimen No. 7-18-1C) showed no bonding since this temperature was well below the melting point of Dacron T-257 fluff pulp. These data establish that synthetic fusible fibers with melting points up to at least about 242 C can be thermobonded when blended with cellulose in low density pads when subject to high frequency electromagnetic radiation.

Although particular embodiments of the present invention have been set forth in the foregoing description, it will be understood by those skilled in the art that the invention is capable of numerous modifications, substitutions and rearrangements without departing from the spirit or essential attributes of the invention. Reference should be made to the appended claims, rather than to the foregoing specification, as indicating the scope of the present invention.

We claim:

1. A process for bonding a blend of cellulosic fluff pulp and fusible synthetic pulp or fiber by dielectric heating, comprising the steps of:
   (a) intimately blending a dry cellulosic fluff pulp with a fusible synthetic pulp or fiber having a melting point less than 250 C, such that the resulting blend comprises between 5-98 parts cellulosic fluff pulp and between 2-95 parts fusible synthetic pulp or fiber and has a density between about 0.005 and about 0.50 g/cc; and
   (b) dielectrically heating the resulting blend in order to bond the blend in less than 15 seconds without the aid of any dielectric sensitizing material.

2. The process according to claim 1 further comprising the step of adding up to about 30 parts of a super absorbent polymer to the resulting blend before it is dielectrically heated.

3. The process according to claim 1 wherein the fusible synthetic pulp or fiber is selected from the group consisting of polyethylene, polypropylene, polyvinyl alcohol, polyester, 6 nylon and 6,6 nylon.

4. The process according to claim 1 wherein the cellulosic fluff pulp comprises wood pulp, cotton linters or cellulose fibers.

5. The process according to claim 1 wherein the resulting blend is dielectrically heated by applying RF energy or microwave energy.

6. The process according to claim 5 wherein between 70 and 2500 MHz of RF energy are applied to dielectrically heat the resulting blend.

7. A dielectrically bonded article having a density between about 0.005 and about 0.50 g/cc comprising:
   (a) 5-98 parts of a cellulosic fluff pulp;
   (b) 2-95 parts of a fusible synthetic pulp or fiber having a melting point less than 250 C; and
   wherein the tensile strength of the interior portion of the bonded article is at least 120% greater than the tensile strength of any surface portion of the bonded article.

8. The article according to claim 7 wherein the article further comprises up to 30 parts of a super absorbent polymer.

9. The article according to claim 7 wherein the fusible synthetic pulp or fiber is selected from the group consisting of polyethylene, polypropylene, polyvinyl alcohol, polyester, 6 nylon and 6,6 nylon.

10. The article according to claim 7 wherein the cellulosic fluff pulp comprises wood pulp, cotton linters or cellulose fibers.

11. The article according to claim 7 wherein the article comprises an absorptive core of a baby diaper, an adult incontinence product or a feminine pad.

12. The article according to claim 7 wherein the article comprises furniture padding, cushioning material or a polishing pad.

* * * * *